United States Patent [19]
Hicks

[11] Patent Number: 5,830,196
[45] Date of Patent: Nov. 3, 1998

[54] TAPERED AND REINFORCED CATHETER

[75] Inventor: Allen J. Hicks, Woodinville, Wash.

[73] Assignee: Tyco Group S.a.r.l., Luxembourg

[21] Appl. No.: 710,697

[22] Filed: Sep. 19, 1996

[51] Int. Cl.⁶ ............................................. A61M 25/00
[52] U.S. Cl. ................................... 604/280; 604/284
[58] Field of Search .................................. 604/282, 280, 604/284

[56] References Cited

U.S. PATENT DOCUMENTS

| | | | |
|---|---|---|---|
| Re. 31,873 | 4/1985 | Howes | 128/674 |
| 3,314,430 | 4/1967 | Alley et al. | 128/350 |
| 3,359,974 | 12/1967 | Khalil | 128/2.05 |
| 3,394,705 | 7/1968 | Abramson | 128/349 |
| 3,437,088 | 4/1969 | Bielinski | 128/2 |
| 3,593,713 | 7/1971 | Bogoff et al. | 128/246 |
| 3,612,050 | 10/1971 | Sheridan | 128/214.4 |
| 3,726,281 | 4/1973 | Norton et al. | 128/349 R |
| 3,746,003 | 7/1973 | Blake et al. | 128/349 B |
| 3,828,767 | 8/1974 | Spiroff | 128/2.05 |
| 3,995,623 | 12/1976 | Blake et al. | 128/2.06 E |
| 4,004,588 | 1/1977 | Alexander | 128/241 |
| 4,100,246 | 7/1978 | Frisch | 264/230 |
| 4,134,402 | 1/1979 | Mahurkar | 128/214 R |
| 4,168,703 | 9/1979 | Kenigsberg | 128/748 |
| 4,180,068 | 12/1979 | Jacobsen et al. | 128/214 R |
| 4,202,332 | 5/1980 | Tersteegen et al. | 128/214.4 |
| 4,257,416 | 3/1981 | Prager | 128/214 R |
| 4,327,722 | 5/1982 | Groshong et al. | 128/214.4 |
| 4,385,631 | 5/1983 | Uthmann | 604/284 |
| 4,403,983 | 9/1983 | Edelman et al. | 604/43 |
| 4,406,656 | 9/1983 | Hattler et al. | 604/280 |
| 4,451,252 | 5/1984 | Martin | 604/43 |
| 4,484,585 | 11/1984 | Baier | 128/748 |
| 4,493,696 | 1/1985 | Uldall | 604/43 |
| 4,543,087 | 9/1985 | Sommercorn et al. | 604/43 |
| 4,559,046 | 12/1985 | Groshong et al. | 604/282 |
| 4,568,329 | 2/1986 | Mahurkar | 604/43 |
| 4,583,968 | 4/1986 | Mahurkar | 604/43 |
| 4,619,643 | 10/1986 | Bai | 604/43 |
| 4,626,240 | 12/1986 | Edelman et al. | 604/43 |
| 4,643,711 | 2/1987 | Bates | 604/4 |
| 4,682,978 | 7/1987 | Martin | 604/43 |
| 4,692,141 | 9/1987 | Mahurkar | 604/43 |

(List continued on next page.)

FOREIGN PATENT DOCUMENTS

| | | |
|---|---|---|
| 1092927 | 1/1981 | Canada . |
| 1150122 | 7/1983 | Canada . |
| 0 036 642 | 9/1981 | European Pat. Off. . |
| 0 079 719 | 5/1983 | European Pat. Off. . |
| 0 333 308 | 9/1989 | European Pat. Off. . |
| 1 285 953 | 7/1962 | France . |
| 1 508 959 | 1/1968 | France . |
| 2 297 640 | 8/1976 | France . |
| 2 530 958 | 2/1984 | France . |
| 2 259 865 | 6/1974 | Germany . |
| WO 84/04043 | 10/1984 | WIPO . |

*Primary Examiner*—Michael Powell Buiz
*Assistant Examiner*—Julian W. Woo
*Attorney, Agent, or Firm*—Richard D. Allison; Montgomery W. Smith

[57] ABSTRACT

A tapered single or multi-lumen catheter having an elongated cylindrical tube for injection and removal of fluid is provided with generally constant or gradually increasing diameter internal lumen or lumens which are connected to a tip portion which may be a conical tapered tip that smoothly merges with the cylindrical surface of the tube so that insertion trauma and the possibility of kinking are minimized. The catheter body is generally formed of proximal and distal portions wherein the proximal portion preferably includes a portion which increases in external diameter in the proximal direction to provide a strain relief for the intersection of the catheter body and the hub member of the catheter. The portion of the catheter body which increases in diameter may also include one or more lumens therein which similarly increase in diameter to increase the flow of fluid therethrough or which are of constant diameter such that the outer wall of the catheter body increases in thickness therealong to increase the columnar strength of the catheter body therealong.

24 Claims, 4 Drawing Sheets

U.S. PATENT DOCUMENTS

| | | | |
|---|---|---|---|
| 4,753,640 | 6/1988 | Nichols et al. | 604/247 |
| 4,772,268 | 9/1988 | Bates | 604/174 |
| 4,795,439 | 1/1989 | Guest | 604/43 |
| 4,822,345 | 4/1989 | Danforth | 604/282 |
| 4,894,057 | 1/1990 | Howes | 604/280 |
| 4,995,865 | 2/1991 | Gahara et al. | 604/43 |
| 5,057,073 | 10/1991 | Martin | 604/43 |
| 5,221,255 | 6/1993 | Mahurkar et al. | 604/43 |
| 5,221,256 | 6/1993 | Mahurkar | 604/43 |
| 5,330,449 | 7/1994 | Prichard et al. | 604/282 |
| 5,348,536 | 9/1994 | Young et al. | 604/43 |
| 5,480,380 | 1/1996 | Martin | 604/284 |

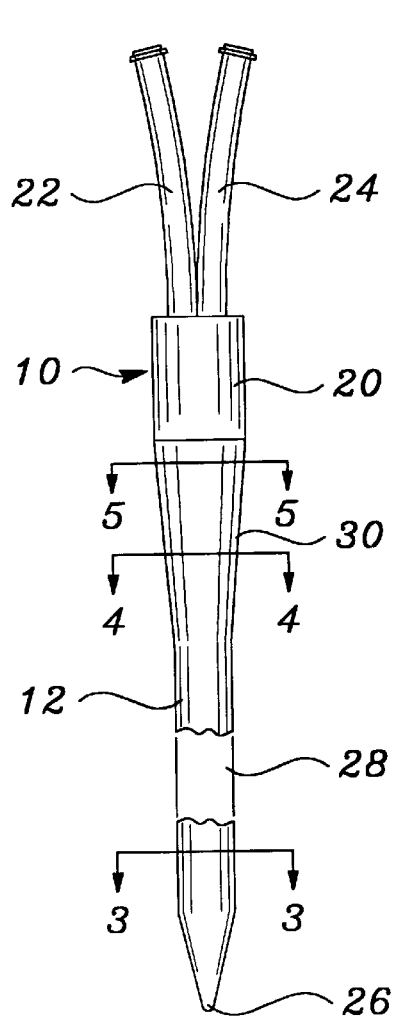
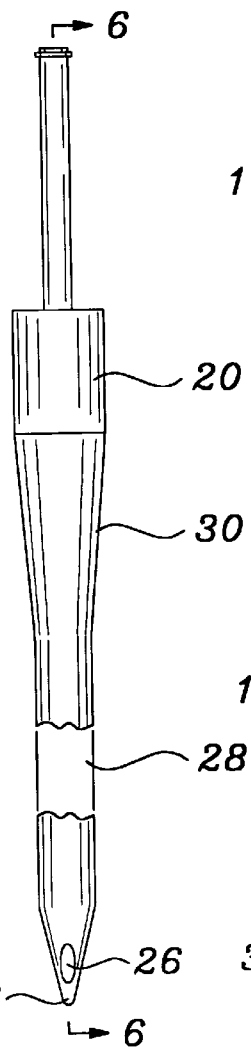
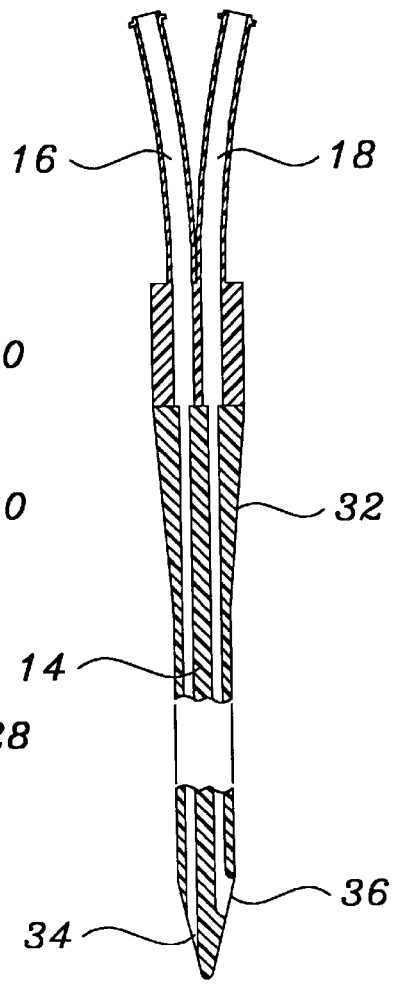
figure 1     figure 2     figure 6
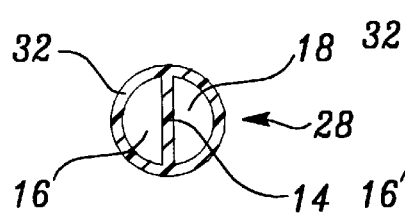
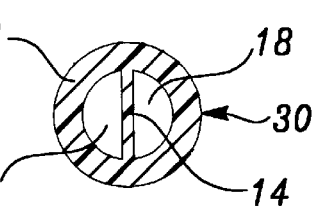
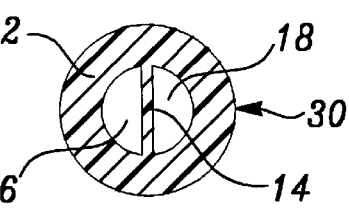
figure 3     figure 4     figure 5

TAPERED AND REINFORCED CATHETER

BACKGROUND OF THE INVENTION

1. Field of the Invention

The present invention relates to surgical instruments for withdrawing fluids from or introducing fluids into cavity of the body such as through multi-lumen catheters for use in extracorporeal or other medical procedures.

2. Description of the Related Art

As is well known, a catheter is a tubular, flexible, surgical instrument for withdrawing fluids from (or introducing fluids into) a cavity of the body. A double-lumen catheter is a catheter having two lumens—one for injection and one for removal of fluid or both lumens for either injection or fluid removal as needed. As is well known, a double-lumen catheter may be used for removing blood from a fistula or vein for processing in a dialysis machine and returning the processed blood back to the fistula or vein. A double-lumen catheter suitable for this purpose is disclosed in Mahurkar, U.S. Pat. No. 4,134,402 issued Jan. 16, 1979. Mahurkar U.S. Pat. No. 4,134,402 discloses a double lumen continuous flow hemodialysis needle and cannula having contiguous lumens of different lengths formed by dividing a unitary straight tube, the shorter lumen acting as a blood intake lumen and the longer acting as a blood return lumen. Semicircular lumens provide a minimal resistance to blood flow resulting in a smaller but highly efficient catheter in comparison to a coaxial double-current catheter. Hemodialysis requires, for example, a blood flow rate of about 200 ml/min. or more and flow resistance less than about 100 mm of mercury.

Mahurkar, U.S. Pat. No. Des. 272,651 issued Feb. 14, 1984, discloses a double lumen catheter having an outlet lumen which has an opening at the tip of the catheter and a shorter inlet lumen which terminates in a bevel substantially displaced from the tip.

Mahurkar, U.S. Pat. No. 4,583,968 issued Apr. 22, 1986, discloses a double lumen catheter having an outlet lumen which has an opening at the tip of the smooth conical tip member and a shorter inlet lumen which terminates proximally of the tip member. Additionally, the use of a coaxial sleeve at the junction of the tube and the connector is disclosed to provide a strain relief and reduce the likelihood of kinking at the junction.

There are numerous other United States patents disclosing double or multi-lumen catheters for hemodialysis other procedures and evidencing a long-felt need for a small, functionally efficient catheter having a minimum of insertion trauma and potential for clotting and kinking.

The catheters described above are generally directed to the use of a straight cylindrical tube which may be subject to occasional kinking because the portion of the cylindrical tube exiting the body of the patient has the same structural strength as the other portions along thee length of the cylindrical tube. Additionally, the diameter of the internal lumens are also generally kept constant throughout the length of the cylindrical tube to maintain a constant flow pressure, although one form of the present invention maintains the thickness of the outer wall of the catheter constant while increasing the outer diameter of the catheter and the diameter of the internal lumens as described below.

It is therefore desirable to provide an improved catheter which includes a tapered portion generally along the proximal portion of the catheter body to form a strain relief area therealong. Additionally, it is also desirable to provide an improved catheter having one or more internal lumens with a diameter that is greater along the proximal portion of the catheter body than the distal portion of the catheter body to provide reduced pressures while providing increased flows in as small a catheter as possible.

SUMMARY OF THE INVENTION

The primary object of the invention is to provide an efficient single or multi-lumen catheter having minimal insertion trauma and a minimal potential for clotting and kinking.

Another object of the invention is to provide a single or multi-lumen catheter which is an effective dilator for soft tissue and veins and which minimizes kinking during insertion and use.

Yet another object of the invention is to provide a dual lumen catheter which utilizes hub and extension tubing components from a larger diameter catheter to minimize the need to stock multiple sizes of parts for various size catheters while providing the further advantage of minimizing kinking during use.

In accordance with one form of the invention, a dual lumen catheter has a pair of lumens with constant internal diameters while the proximal portion of the catheter body gradually increases in thickness as it approaches the hub member of the catheter to increase the tubular stiffness or columnar strength of the proximal portion of the catheter body. The increased thickness of the material in the walls of the proximal portion of the catheter body increases the columnar strength of the catheter adjacent to hub member of the catheter to form a strain relief area so that the likelihood that the catheter will kink at the intersection of the catheter body and hub member is minimized. Additionally, the gradually increasing external diameter along the proximal portion of the catheter body exponentially strengthens the portion of the catheter body which exits from the body of the patient to minimize kinking at this location also. The present invention also allows the same hub members to be used for small diameter catheters as are used for larger diameter catheters. This feature further decreases the resistance to fluid flow typically present through the extension members and hub member by providing a proportionally larger internal diameter in the hub member and extension members than in the catheter body while also allowing for the lower cost manufacture of the relatively low sales volume smaller catheters by using components which are common to the larger sales volume catheters.

Another effect of the present invention relates to the embodiment which includes tapered lumens along the proximal portion thereof. By tapering the internal lumen of the proximal portion of the catheter body, the volume of fluid or blood that is passed through the catheter body is increased at reduced pressures while still providing the catheter strain relief effect described above. This effect is explained by Pouisuille's equation for flow within a tube where $V=p(d)^4/nl$. in this equation, V=flow, p=pressure, d=tube diameter, n=viscosity and l=length of the tube. Therefore, the ratio of pressure is dependent not only upon the diameter of the tube, but also in a 1:1 ratio with the length of the tube and as the diameter of the internal lumen is increased, the pressure is decreased and the flow increases in proportion to the length of tube having the increased diameter of the internal lumen.

In accordance with one form of the invention, the dual lumen catheter may also have a smooth conical tapered tip that smoothly merges with the distal portion of the catheter body so that insertion of the catheter is facilitated. The conical tip forms a tip guidance point which is located at the center of the conical tip for uniform distribution of frictional resistance and while minimizing insertion trauma and kinking. The conical tapered tip comprises a relative concentration of material to impart relative rigidity so that the tip functions as an effective dilator for soft tissue and veins. Semicircular lumens may also be provided to insure non-static laminar flow and prevent clotting. A double lumen catheter of this type may be particularly advantageous when a tunneling procedure or blind technique must be used, for example, to reach a vein under the collar bone or neck.

In accordance with the present invention, the catheter may also have a single or plural lumens and may increase in external diameter from the approximate lengthwise middle of the catheter body. Additionally, as described above, in one form of the present invention, the diameter of the internal lumen or lumens of the catheter body may increase proportionally with the increased external diameter of the proximal portion of the catheter body so that the wall thickness remains the same or is increased slightly as the intersection with the hub member is reached.

BRIEF DESCRIPTION OF THE DRAWINGS

Other objects and advantages of the invention will become apparent from the following detailed description and the accompanying drawings, in which:

FIG. 1 is a front elevational view of a double lumen catheter according to the present invention;

FIG. 2 is a right side elevational view of the double lumen catheter illustrated in FIG. 1;

FIG. 3 is a view in section of the double lumen catheter illustrated in FIG. 1 taken along line 3—3 thereof;

FIG. 4 is a view in section of the double lumen catheter illustrated in FIG. 1 taken along line 4—4 thereof;

FIG. 5 is a view in section of the double lumen catheter illustrated in FIG. 1 taken along line 5—5 thereof;

FIG. 6 is a view in section of the double lumen catheter illustrated in FIG. 1 taken along line 6—6 shown in FIG. 2;

FIGS. 17, 18 and 19 are views in section showing an alternate cross sectional configuration in a double lumen catheter of the type shown in FIG. 1 wherein FIGS. 17, 18 and 19 are cross sectional configurations taken generally along the same lines as lines 3—3, 4—4 and 5—5 of FIG. 1.

Figures 7, 11:
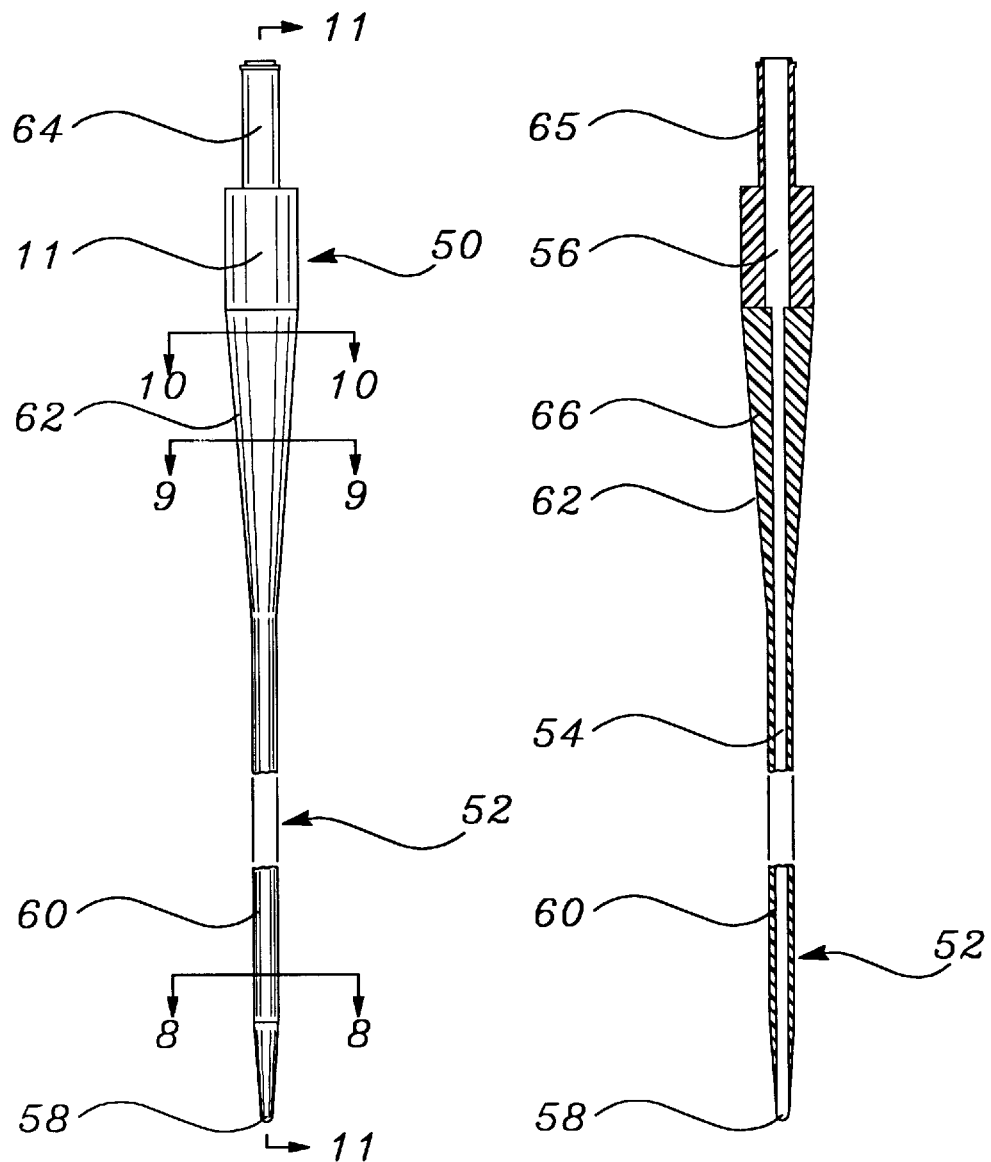
FIG. 7 is a front elevational view of a single lumen catheter according to the present invention.
FIG. 11 is a view in section of the single lumen catheter illustrated in FIG. 7 taken along line 11—11 shown in FIG. 7.

While the invention will be described in connection with a certain preferred embodiment, it will be understood that it is not intended to limit the invention to that particular embodiment. On the contrary, it is intended to cover all alternatives, modifications, and equivalents as may be included within the spirit and scope of the invention as defined by the appended claims.

DETAILED DESCRIPTION OF THE PREFERRED EMBODIMENT

Turning now to the drawings, FIGS. 1–20 show various embodiments of the catheters of the present invention, generally designated as 10, 50 and 70, respectively. As is conventional for a double lumen catheter 10 has an elongated hollow tube or catheter body 12 which is inserted into a cavity of the body such as a fistula or vein. The catheter body 12 is preferably circular in external cross section, as specifically shown in FIGS. 3–5, and has an internal septum 14 defining a return lumen 16 and an inlet lumen 18 within the interior of the catheter body 12. The lumens 14 and 16 of the embodiment shown in FIGS. 1–6 are have a constant diameter and are preferably semicircular or "D" shaped to minimize the resistance to fluid flow. As is conventional for this type of dual lumen construction, the septum 14 extends axially along the catheter body 12 from a hub member 20. The hub member 20 connects the proximal end portions of catheter body 12 including the return lumen 14 and the inlet lumen 16 to respective fluid return and inlet extensions 22 and 24 which are, for example, respective venous and arterial lines or extension members which are connected to a dialysis or similar unit. The proximal side of the hub member 20 connects to the return extension 22 and inlet extension 24 which are then connected to the dialysis or other machine. The preferred direction of fluid circulation when the present invention is used for extra corporeal procedures such as hemodialysis, apherisis or similar applications is indicated by the arrows in FIG. 1.

Figure 20:
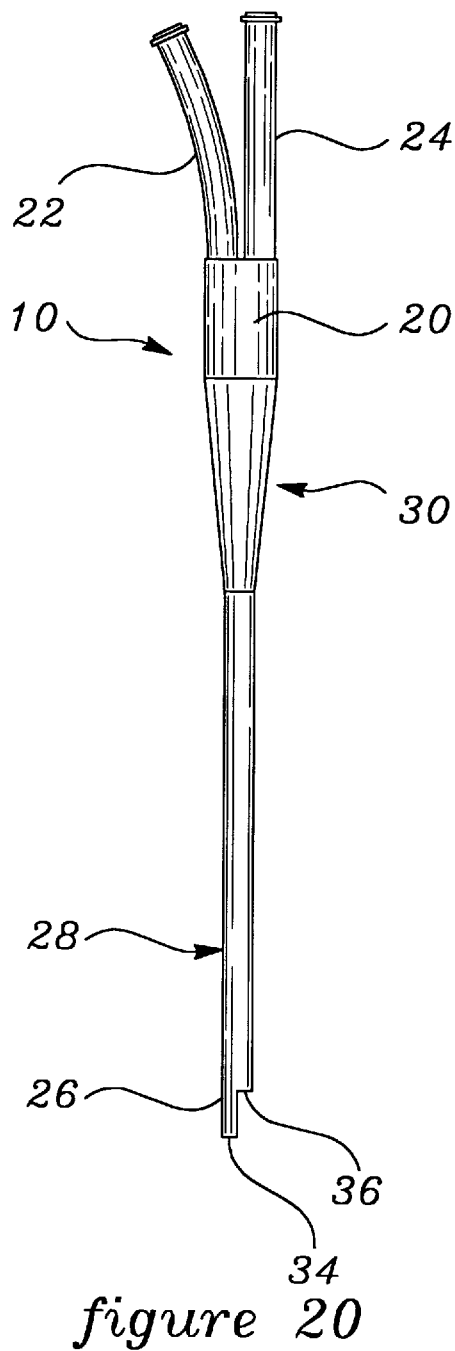
FIG. 20 is a front elevational view of an alternate form of a double lumen catheter according to the present invention.

As best shown in FIG. 6, the catheter body 12 generally includes a tip portion 26 which is connected to the distal end of the distal portion 28 of the catheter body 12 and a proximal portion 30 which is connected to the distal side of the hub member 20. The diameters of the return and inlet lumens, 16 and 18, are preferably maintained constant along the lengthwise dimension of the catheter body 12 in this embodiment while the thickness of the outer wall 32 of the catheter body 12 is increased. This increase in the thickness of the outer wall 32 provides a strain relief along the proximal portion 30 of the catheter body 12 and is illustrated by comparing FIGS. 3, 4 and 5. Alternately, the diameter of the outer wall 32 may also be increased while maintaining the thickness of the outer wall 32 constant so that the diameter of the return lumen 16 and inlet lumen 18 along the proximal portion 30 of the catheter body 30 are also increased as shown in FIG. 20 to decrease the resistance to the flow of fluid therethrough. This feature, in addition to the ability to use a hub member and extension members having larger internal diameters provides a catheter having an increased flow of fluids while the resistance to the flow of fluids therethrough is reduced.

The distal portion 28 of the catheter body 12 includes openings or apertures at the distal end portions of the lumens to permit the flow of fluid between a body cavity (not shown) and the lumens. The return lumen 16 extends along the entire length of the catheter body 12 to an aperture or opening 34 at the distal end or tip portion 26 of the catheter 10. The inlet lumen 18 is shorter than the return lumen 16 and terminates at its distal end at an aperture or opening 36 that is in the outer wall 32 of the catheter body 12 and is displaced from the opening 34 at the distal end of the catheter 10.

In accordance with a preferred form of the invention, the catheter body 12 is connected to a conical tip portion 26 which smoothly merges with the catheter body 12 at the intersection thereof. Preferably, the apex of the tip portion 26 of this embodiment is centered on the axis of the catheter body 12 of the catheter 10 thus serving as a guidance point to uniformly distribute the frictional resistance encountered by the tip portion 26 when the catheter 10 is inserted into the body cavity (not shown). As shown in FIGS. 1 and FIG. 6, the outer diameter of the distal portion 28 of the catheter body 12 of the catheter 10 converges smoothly at the intersection of the distal portion 28 and the tip portion 26 to form a truncated cone and the return lumen 16 opens at the truncated apex of the cone. As shown, the tip portion 26 of this embodiment preferably has a gradual taper which preferably has a length of approximately two or more diameters of the catheter body 12. Since the frictional resistance to insertion is uniformly distributed and the tip portion 26 smoothly merges with the distal portion 28 of the catheter body 12, insertion trauma and kinking are minimized. The tip portion 26 may also be formed as a blunt tip where the return and inlet lumens open at the same location or a staggered tip where the inlet lumen 18 opens along the lengthwise dimension of the catheter body 12 and the remaining portion of the catheter body 12 distally of the inlet lumen 18 is generally circular and is smaller than the diameter of the portion of the catheter body 12 surrounding the inlet lumen 18 and the return lumen 16.

The conventional use of relatively small return openings 34 and inlet openings 36 also function to reduce insertion trauma, but they also impede fluid flow. Therefore, an additional group of holes or apertures may be used to connect the return lumen 22 to the outer surface of the catheter body 12, and an additional group of holes or apertures may be used to connect the inlet lumen 18 to the outer surface of the catheter body 12. The return holes or apertures may be axially disposed between the base of the tip portion 26 and the inlet aperture 34 at the distal end of the inlet lumen 18. The additional inlet holes or apertures may be axially disposed between the inlet aperture 36 and the proximal end of the catheter body 12. The return holes and the inlet holes are further disposed circumferentially on opposite sides of the septum 14. Thus, there is axial as well as circumferential separation of the inlets and outlets for fluid circulation. Alternately, either or both of the inlet holes and return holes of the present invention may be formed as an elongate slot of the type disclosed in U.S. Pat. No. 5,403,231 wherein the opening may be shaped generally as a parallelogram on the outer wall 32 of the catheter body 12.

As shown in FIG. 6, the tip portion 26 is generally formed with a relatively large concentration of material to provide increased stiffness to the tip portion 26. This stiffening aids penetration of the tip portion 26 into the body cavity (not shown) and also aids the dilation of soft tissue such as veins. The tip portion 26 as shown in FIG. 6 is preferably formed from a material such as a thermo-plastic material. The tip portion 26 including the relative concentration of material is readily molded and bonded or is integrally formed from the cylindrical catheter body 12 by the use of internal and external mandrels and the application of heat by any number of conventional means such as RF forming, thermal forming or infrared forming.

For use in hemodialysis type procedures, the double lumen catheter 10 is introduced in the direction of blood flow in a large vein over a hypodermic needle or Seldinger's guide wire, or through a sheath as is conventional. The side opening 36 on the blood inlet lumen 18 draws the blood for processing by a hemodialysis, apherisis or similar machine and the processed blood is returned through the return lumen 16 and out through the opening 34 to return the blood upstream into circulation. The geometrical properties of the double lumen catheter as shown in the drawing figures insure that insertion trauma, kinking, and the possibility of clotting are minimized during use including hemodialysis procedures.

Figures 8, 9, 10:
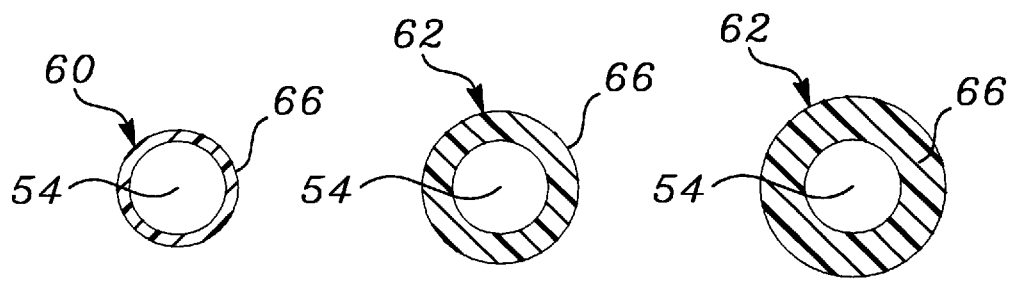
FIG. 8 is a view in section of the single lumen catheter illustrated in FIG. 7 taken along line 8—8 thereof.
FIG. 9 is a view in section of the single lumen catheter illustrated in FIG. 7 taken along line 9—9 thereof.
FIG. 10 is a view in section of the single lumen catheter illustrated in FIG. 7 taken along line 10—10 thereof.

As shown in FIGS. 7–11, the catheter 50 of this alternate embodiment is a single lumen catheter having a catheter body 52 which is preferably circular in external cross section, as specifically shown in FIGS. 8–10. The lumen 54 of the embodiment shown in FIGS. 7–11 has a generally constant diameter and is shaped to minimize the resistance to fluid flow. As is conventional for this type of single lumen catheter, the catheter body 52 extends between a hub member 56 and the tip portion 58. The hub member 56 connects the proximal end portion of catheter body 52 and includes an extension member 64 which may then be connected to an external device or unit.

As best shown in FIG. 11, the catheter body 52 generally includes the tip portion 58 which is connected to the distal end of a distal portion 60 of the catheter body 52 and a proximal portion 62 which connected to the distal side of the hub member 56. In this embodiment, the diameter of the lumen 54 is preferably maintained generally constant along the lengthwise dimension of the catheter body 52 while the thickness of the outer wall 66 of the catheter body 52 is increased. This increase in the thickness of the outer wall 66 provides a strain relief along the proximal portion 62 of the catheter body 52 and is illustrated by comparing FIGS. 8, 9 and 10. Alternately, the diameter of the outer wall 66 may be increased while maintaining the thickness of the outer wall 66 constant so that the diameter of the lumen 54 is also increased in the manner shown in the embodiment of FIG. 20. Additionally, although the tip portion 58 of this embodiment is shown as being generally conical, blunt or staggered tip portions as described above may also be used with the present embodiment.

Figures 12, 16:
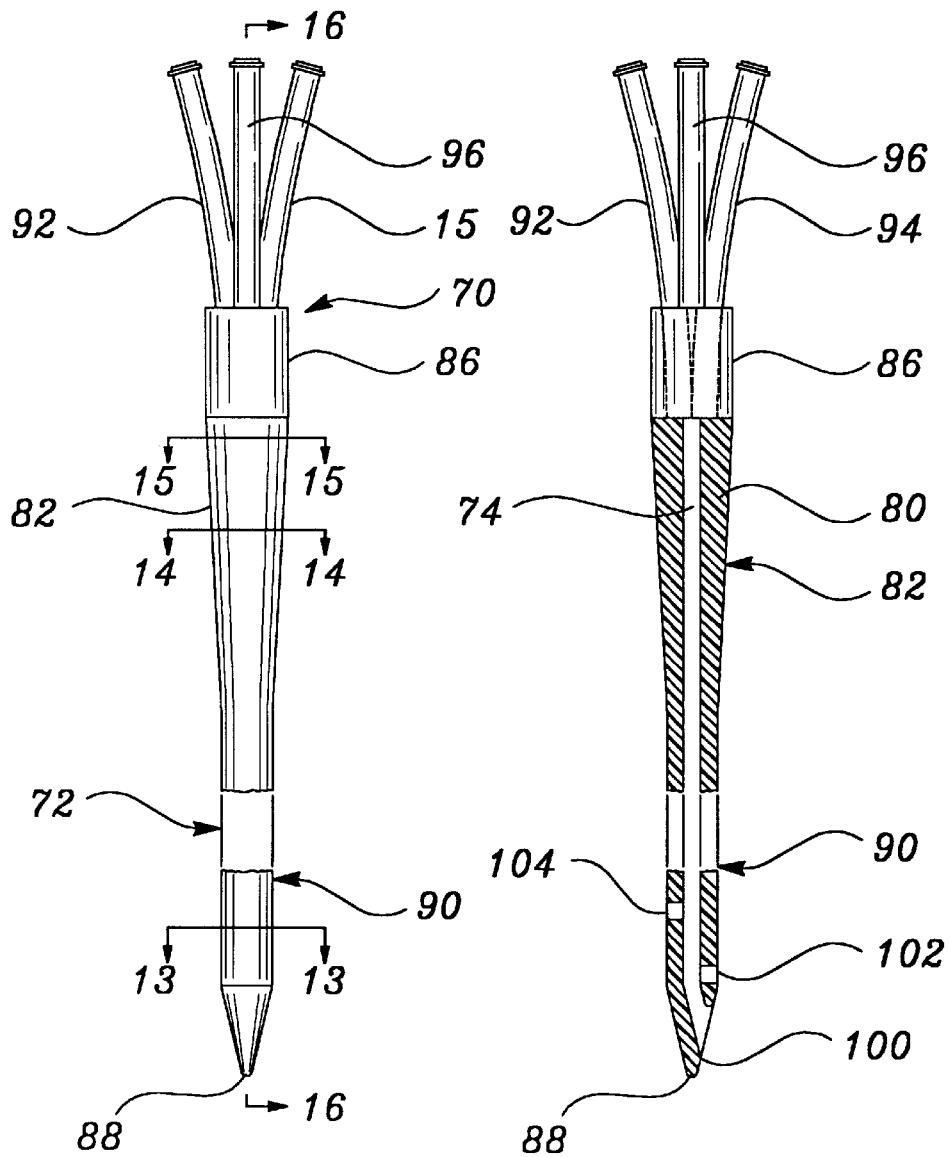
FIG. 12 is a front elevational view of a triple lumen catheter according to the present invention.
FIG. 16 is a view in section of the triple lumen catheter illustrated in FIG. 12 taken along line 16—16 shown in FIG. 12.
Figures 13, 14, 15:
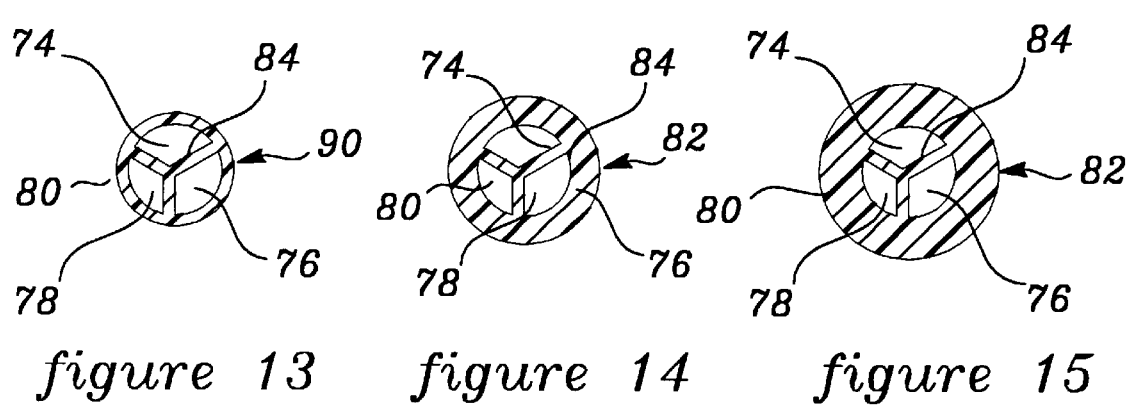
FIG. 13 is a view in section of the triple lumen catheter illustrated in FIG. 12 taken along line 13—13 thereof.
FIG. 14 is a view in section of the triple lumen catheter illustrated in FIG. 12 taken along line 14—14 thereof.
FIG. 15 is a view in section of the triple lumen catheter illustrated in FIG. 12 taken along line 15—15 thereof.

As shown in FIGS. 12–16, the catheter 70 of this alternate embodiment is a triple lumen catheter having a catheter body 72 which is preferably circular in external cross section, as specifically shown in FIGS. 13–15. The lumens 74, 76, and 78 of the embodiment shown in FIGS. 12–16 also have a generally constant diameter with an outer wall 80 which gradually increases in thickness proximally along the proximal portion 82 of the catheter body 72 and are shaped to minimize the resistance to fluid flow therethrough.

The catheter body 72 of this embodiment is preferably circular in external cross section, as shown in FIGS. 13–15, and has an internal septum 84 defining first, second and third lumens, 74, 76, and 78 respectively, within the interior of the catheter body 72. The lumens 74, 76 and 78 of the embodiment shown in FIGS. 12–16 preferably have a constant diameter and the first lumen 74 and second lumen 76 are preferably larger in diameter than the third lumen 78 and are generally semicircular or "D" shaped to minimize the resistance to fluid flow therethrough. As is conventional for this type of triple lumen catheter 70, the septum 84 extends axially along the catheter body 72 from a hub member 86 to a tip portion 88 on the distal portion 90 of the catheter body 72. The hub member 86 securely connects the proximal portion 82 of catheter body 72 including the first, second and third lumens 84, 86 and 88 to respective extensions members 92, 94 and 96 which are in flow communication with their respective lumens through the hub member 86. The proximal side of the hub member is connected to the extension members 92, 94 and 96 which are then connected to the external unit or device.

As best shown in FIG. 16, the catheter body 72 generally includes a tip portion 98 which is connected to the distal end of the distal portion 90 of the catheter body 72 and a proximal portion 82 which is connected to the distal side of the hub member 86. The diameter of the respective lumens, 74, 76 and 78, are preferably maintained constant along the lengthwise dimension of the catheter body 72 in this embodiment while the thickness of the outer wall 80 of the catheter body 72 is increased. This increase in the thickness of the outer wall 80 provides a strain relief along the proximal portion 82 of the catheter body 72 to resist bending or kinking along the intersection of the catheter body 72 and the hub member 86 and is illustrated by comparing FIGS. 13, 14 and 15. Alternately, the diameter of the outer wall 80 may be increased while maintaining the thickness of the outer wall 80 constant so that the diameter of the first, second and/or third lumens may be increased as desired generally in the manner shown in FIG. 18.

The distal portion 90 of the catheter body 72 of this embodiment includes openings or apertures at the distal end portions of the lumens to permit the flow of fluid between a body cavity (not shown) and the lumens. The first lumen 74 extends along the entire length of the catheter body 72 to an aperture or opening 100 at the distal end or tip portion 88 of the catheter 70. The second lumen 76 is preferably shorter than the first lumen 74 and terminates at its distal end at an aperture or opening 102 that is in the outer wall 80 of the catheter body 72 and is displaced proximally from the opening 100 at the distal end of the catheter 70. The third lumen 78 is preferably shorter than the first lumen 74 and the second lumen 76 and preferably terminates at its distal end at an aperture or opening 104 that is in the outer wall 80 of the catheter body 72. The opening for the third lumen 78 is preferably displaced proximally and axially from the opening 102 of the second lumen 76.

Figure 17:
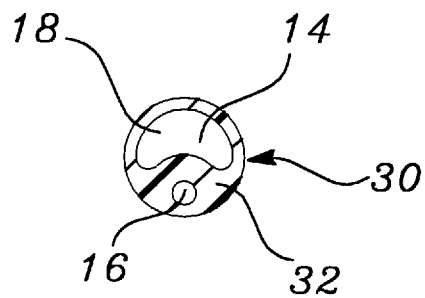
Figure 18:
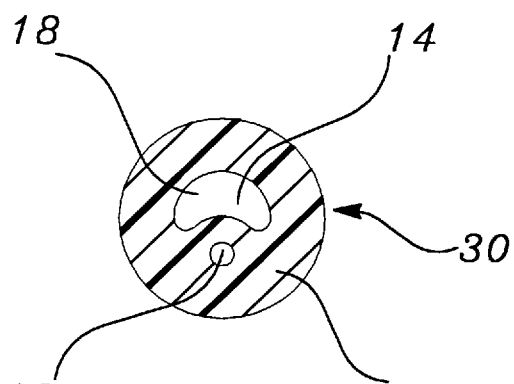
Figure 19:
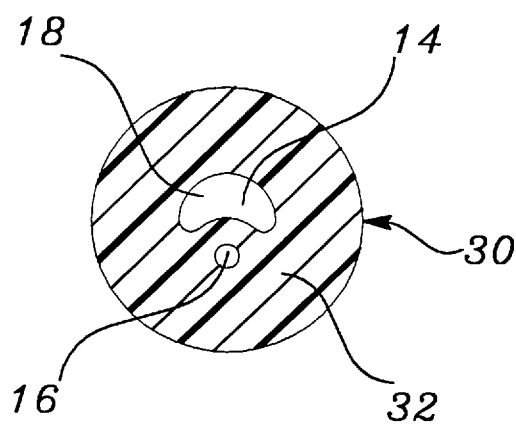

FIGS. 17, 18 and 19 are illustrative of a dual lumen catheter which is similar in side view to the catheter shown in FIG. 1 and therefore, like numbers have been added to like members. The catheter body 12 of this embodiment is preferably circular in external cross section and has an internal septum 14 defining a return lumen 16 and an inlet lumen 18 within the interior of the catheter body 12. The lumens 14 and 16 of the embodiment shown in FIGS. 17–19 preferably have a constant diameter and are preferably shaped to include a generally circular return lumen 16 and an oblong or tear drop shaped inlet lumen 18. As is conventional for this type of dual lumen construction, the septum 14 extends axially along the catheter body 12 from a hub member (not shown). The hub member connects the proximal end portions of catheter body 12 including the return lumen 14 and the inlet lumen 16 to respective fluid return and inlet extensions (not shown) which are, for example, respective venous and arterial lines or extension members which are connected to a dialysis or similar unit. The proximal side of the hub member connects to the return extension and inlet extension which are then connected to the dialysis or other external machine or device.

The diameter of the return and inlet lumens, 16 and 18, of this embodiment is preferably maintained constant along the lengthwise dimension of the catheter body 12 while the thickness of the outer wall 32 of the catheter body 12 is increased. This increase in the thickness of the outer wall 32 provides a strain relief along the proximal portion 30 of the catheter body 12 and is illustrated by comparing FIGS. 17, 18 and 19. Alternately, the diameter of the outer wall 32 may be increased while maintaining the thickness of the outer wall 32 constant so that the diameter of the return lumen 16 and inlet lumen 18 along the proximal portion 30 of the catheter body 30 are also increased as shown in FIG. 20 to provide a decrease in the resistance to the flow of fluid therethrough.

What is claimed is:

1. A catheter comprising an elongated cylindrical tube having a longitudinal interior lumen, said tube having distal and proximal portions and a tip member on the distal end of said distal portion and said proximal portion of said cylindrical tube connecting to a hub member and said hub member connecting to at least one separate extension member and said at least one extension member communicating with said lumen via said hub member for the injection and removal of fluid through said cylindrical tube, said cylindrical tube having an external diameter wherein said diameter of said distal portion is generally uniform and said diameter of said proximal portion increases in diameter in the proximal direction thereof such that said diameter of said cylindrical tube is greater adjacent to said hub member than said diameter of said distal portion; and wherein said cylindrical tube includes at least one septum extending longitudinally therethrough to form a plurality of lumens therein and said lumens each having a diameter which is greater adjacent to said hub member than said diameter of said lumens in said distal portion of said cylindrical tube.

2. The catheter of claim 1, wherein said lumen of said cylindrical tube includes a diameter which is generally uniform throughout the lengthwise dimension thereof.

3. The catheter of claim 1, wherein said cylindrical tube includes a diameter which is greater adjacent to said hub member than said diameter of said lumen in said distal portion of said cylindrical tube.

4. The catheter of claim 1, wherein said cylindrical tube includes at least one septum extending longitudinally therethrough to form a plurality of lumens therein and said lumens each having a diameter which is generally uniform throughout the lengthwise dimension thereof.

5. The catheter of claim 1, wherein said cylindrical tube includes first and second lumens therein and said first lumen extends lengthwise along said cylindrical tube and said tip member and said second lumen terminates at an opening in the side of said cylindrical tube.

6. The catheter of claim 1, wherein said tip member includes an apex thereon and said apex of said tip member is substantially aligned with the axis of said cylindrical tube.

7. The catheter of claim 1, wherein the length of said tip member is at least approximately two diameters of said cylindrical tube.

8. The catheter of claim 1, wherein said cylindrical tube includes first and second lumens therein and said first and second lumens are of semicircular cross sectional shape.

9. The catheter of claim 1, wherein said cylindrical tube includes first and second lumens therein and said first and second lumens are of different cross sectional shape.

10. A multiple lumen catheter comprising an elongated cylindrical tube including an axial divider bisecting said cylindrical tube into first and second lumens and including proximal and distal portions thereof and said proximal portion is connected to a hub member and said distal portion is connected to a tip member, said proximal end of said proximal portion of said cylindrical tube connecting two separate extension members communicating with the respective first and second lumens via said hub member for the injection and removal of fluid, said first lumen extending from said proximal portion of said cylindrical tube to a first opening at the distal end of said distal portion of said cylindrical tube, said second lumen extending from the proximal portion of said cylindrical tube to a second opening in the side of said cylindrical tube, said second lumen terminating at said second opening and said cylindrical tube having a diameter adjacent to said hub member which is greater than the diameter of said cylindrical tube along said distal portion thereof; and wherein said second lumen has a diameter which is greater adjacent to the hub member than the diameter along the length of said distal portion.

11. The multiple lumen catheter of claim 10, wherein said first lumen has a diameter which is generally uniform along the length thereof.

12. The multiple lumen catheter of claim 10, wherein said first lumen and said second lumen have a diameter which is generally uniform along the length of said cylindrical tube.

13. The multiple lumen catheter of claim 10, wherein said tip member is generally conical and includes a length which is at least approximately two diameters of said cylindrical tube.

14. The multiple lumen catheter of claim 10, wherein said second lumen opens at an opening in the side of said cylindrical tube and said tip member includes said first lumen extending therethrough.

15. The multiple lumen catheter of claim 10, wherein the diameter of said first lumen along said distal portion is generally uniform.

16. A double lumen catheter comprising an elongated unitary cylindrical tube having distal and proximal portions and including an integral septum extending axially along the entire length of the tube and dividing the interior of said tube into a first and second lumen, the outer circumference of said tube is generally uniform along said distal portion thereof and gradually increasing in the proximal direction from the intersection of said distal portion and said proximal portion and said distal portion including a distal end having a tip member thereon and said proximal portion having a hub member thereon and said hub member having a plurality of lumens therein in fluid flow communication with said first and second lumens of said cylindrical tube; and wherein said first lumen includes a first diameter adjacent to said hub member and a second diameter along said distal portion of said cylindrical tube and said first diameter is greater than said second diameter.

17. The double lumen catheter of claim 16, wherein said cylindrical tube includes a outer wall having a generally uniform thickness along the entire length thereof.

18. A double lumen catheter comprising an elongated unitary cylindrical tube having distal and proximal portions and including an integral septum extending axially along the entire length of the tube and dividing the interior of said tube into a first and second lumen and the diameter of said first lumen is generally uniform along said distal portion of said cylindrical tube and gradually increasing in the proximal direction from the intersection of said distal portion and said proximal portion of said cylindrical tube and said distal portion including a distal end having a tip member thereon and said proximal portion having a hub member thereon and said hub member having a plurality of lumens therein in fluid flow communication with said first and second lumens of said cylindrical tube.

19. The double lumen catheter of claim 18, wherein said cylindrical tube includes a first diameter adjacent to said hub member and a second diameter along said distal portion of said cylindrical tube and said first diameter is greater than said second diameter.

20. The double lumen catheter of claim 18, wherein said cylindrical tube includes a outer wall having a generally uniform thickness along the entire length thereof.

21. A catheter comprising an elongated cylindrical tube having a longitudinal interior lumen and a hum member having a longitudinal interior lumen, said tube having distal and proximal portions and a tip member on the distal end of said distal portion and said proximal portion of said cylindrical tube connecting to said hub member and said hub member connecting to at least one separate extension member and said at least one extension member communicating with said tube lumen via said hub member lumen for the injection and removal of fluid through said cylindrical tube, said cylindrical tube having an external diameter wherein said diameter of said distal portion is generally uniform and said diameter of said proximal portion increases in diameter in the proximal direction thereof such that said diameter of said cylindrical tube is greater adjacent to said hub member than said diameter of said distal portion and said hub member lumen having a diameter greater than the diameter of the tube lumen; and wherein said tip member includes a conical tapered tip member formed of a concentration of material exceeding the concentration of material which forms the cylindrical body of said cylindrical tube.

22. A multiple lumen catheter comprising an elongated cylindrical tube including an axial divider bisecting said cylindrical tube into first and second lumens and including proximal and distal portions thereof and said proximal portion is connected to a hub member and said distal portion is connected to a tip member, said proximal end of said proximal portion of said cylindrical tube connecting two separate extension members communicating with the respective first and second lumens via said hub member for the injection and removal of fluid, said first lumen extending from said proximal portion of said cylindrical tube to a first opening at the distal end of said distal portion of said cylindrical tube, said second lumen extending from the proximal portion of said cylindrical tube to a second opening in the side of said cylindrical tube, said second lumen terminating at said second opening and said cylindrical tube having a diameter adjacent to said hub member which is greater than the diameter of said cylindrical tube along said distal portion thereof; and wherein said first lumen and said second lumen have a diameter which is greater adjacent to the hub member than the diameter along the length of said distal portion.

23. A multiple lumen catheter comprising an elongated cylindrical tube including an axial divider bisecting said cylindrical tube into first and second lumens and including proximal and distal portions thereof and said proximal portion is connected to a hub member and said distal portion is connected to a tip member, said proximal end of said proximal portion of said cylindrical tube connecting two separate extension members communicating with the respective first and second lumens via said hub member for the injection and removal of fluid, said first lumen extending from said proximal portion of said cylindrical tube to a first opening at the distal end of said distal portion of said cylindrical tube, said second lumen extending from the proximal portion of said cylindrical tube to a second opening in the side of said cylindrical tube, said second lumen terminating at said second opening and said cylindrical tube having a diameter adjacent to said hub member which is greater than the diameter of said cylindrical tube along said distal portion thereof; and wherein the diameter of said first lumen gradually increases in the proximal direction from the intersection of said distal portion and said proximal portion of said cylindrical tube to the intersection of said proximal portion and said hub member.

24. The multiple lumen catheter of claim 23 wherein the thickness of said cylindrical tube is generally uniform.

* * * * *

UNITED STATES PATENT AND TRADEMARK OFFICE
CERTIFICATE OF CORRECTION

PATENT NO. : 5,830,196
DATED : November 3, 1998
INVENTOR(S) : Allen J. Hicks

It is certified that error appears in the above-identified patent and that said Letters Patent is hereby corrected as shown below:

On the Title page, insert the following:

--[60] Provisional application No. 60/004,071, filed Sept. 21, 1995--

Column 1, line 2, insert the following:

--CROSS REFERENCE TO RELATED APPLICATION
Reference is made to and priority claimed from U.S. provisional application Ser. No. 60/004,071, filed Sept. 21, 1995, entitled TAPERED AND REINFORCED CATHETER--

Signed and Sealed this

Ninth Day of May, 2000

Attest:

Q. TODD DICKINSON

*Attesting Officer*          *Director of Patents and Trademarks*